United States Patent [19]

Olness et al.

[11] Patent Number: 4,906,917
[45] Date of Patent: Mar. 6, 1990

[54] ELASTOMER DEGRADATION SENSOR USING A PIEZOELECTRIC MATERIAL

[75] Inventors: Dolores U. Olness, Livermore; Tomas B. Hirschfeld, deceased, late of Livermore, both of Calif., by Judith Hirschfeld, Administratrix

[73] Assignee: The United States of America as represented by the United States Department of Energy, Washington, D.C.

[21] Appl. No.: 359,463

[22] Filed: Jun. 1, 1989

[51] Int. Cl.$^4$ .................. G01R 31/00; H01L 41/08
[52] U.S. Cl. .................................. 324/623; 324/557; 310/327
[58] Field of Search ............... 324/56, 57 Q, 551, 554, 324/557; 73/575, 577, 579, 768, 775, 778, 866; 310/327, 345, 321-323, 340

[56] References Cited

U.S. PATENT DOCUMENTS 3,269,175  8/1966  Sprosty ........................ 73/575 X
3,401,276  9/1968  Curran et al. .................. 310/327 X Primary Examiner—Reinhard J. Eisenzopf
Assistant Examiner—Jack B. Harvey
Attorney, Agent, or Firm—Henry P. Sartorio; L. E. Carnahan; William R. Moser

[57] ABSTRACT

A method and apparatus for monitoring the degradation of elastomeric materials is provided. Piezoelectric oscillators are placed in contact with the elastomeric material so that a forced harmonic oscillator with damping is formed. The piezoelectric material is connected to an oscillator circuit,. A parameter such as the resonant frequency, amplitude or Q value of the oscillating system is related to the elasticity of the elastomeric material. Degradation of the elastomeric material causes changes in its elasticity which, in turn, causes the resonant frequency, amplitude or Q of the oscillator to change. These changes are monitored with a peak height monitor, frequency counter, Q-meter, spectrum analyzer, or other measurement circuit. Elasticity of elastomers can be monitored in situ, using miniaturized sensors.

16 Claims, 5 Drawing Sheets

ELASTOMER DEGRADATION SENSOR USING A PIEZOELECTRIC MATERIAL

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates to method and apparatus for measuring changes in the elasticity of materials, particularly elastomers used for gaskets, seals, and the like, particularly in situ measurements.

The elasticity of a material is an important property and its loss or degradation can have serious consequences, ranging from changes in mechanical or electrical properties to catastrophic failure. The industrial and military use of elastic materials for gaskets and seals is ubiquitous. The gasket and sealant materials are typically subjected to extraordinary variations in stress, vibration, temperature, and exposure to various chemical agents, which lead to eventual degradation of elasticity and failure of the materials. In most situations, gasket and sealant failure can lead to costly maintenance, and prolonged downtime if the failure is not rapidly detected or anticipated. In the extreme case, gasket or seal failure can have catastrophic results, as evidenced by the space shuttle disaster.

Currently, there are no convenient or practical means for in situ monitoring of the state of elastomer degradation in gaskets, seals, or the like, when used in industrial equipment or vehicles. In particular, because in situ monitors are currently not available, either the gasket or sealant materials must be removed from the equipment for inspection and testing, or the materials must be routinely replaced at intervals determined by theoretical estimates of failure times.

Clearly the availability of an inexpensive in situ monitor of gasket and sealant elasticity would result in significant savings in time and money by eliminating unnecessary maintenance, and by avoiding the consequences of unanticipated failures of the gasket or sealant materials.

SUMMARY OF THE INVENTION

It is therefore an object of the invention to provide an in situ sensor for monitoring the elasticity of elastomeric materials.

A more specific object of the invention is to provide miniature piezoelectric-based sensors embedded in, or in contact with, elastic materials used as gaskets or sealants in industrial equipment or vehicles.

Additional objects, advantages and novel features of the invention will be set forth in part in the description which follows, and in part will become apparent to those skilled in the art upon examination of the invention. The objects and advantages of the invention may be realized and attained by means of the instrumentalities and combinations particularly pointed out in the appended claims.

These and other objects are achieved in accordance with the invention by providing one or more miniature piezoelectric oscillators in contact with the elastomer whose elasticity is to be monitored, typically with the elastomer in situ. The piezoelectric oscillator in contact with the elastomer is essentially a forced harmonic oscillator with damping. The elastomer provides the damping; the greater the elasticity, the greater the damping. Such a system has a resonance frequency which is a sensitive function of the size, shape, and nature of the piezoelectric material of the oscillator, and the elasticity of the elastomer, i.e., the gasket or sealant material. The resonant frequency is the frequency at which the driving force causes maximum displacement of the oscillating system. For piezoelectric oscillators, very small deviations in driving frequency from resonance or very small changes in oscillator properties (e.g., damping) result in large changes in amplitude, i.e., the piezoelectric oscillators are characterized by very high Q values. Thus in practice a piezoelectric oscillator oscillates only at or very near resonance.

Both the amplitude and resonant frequency are sensitive to various oscillator properties, including damping provided by the in situ elastomer. Since the vibrational characteristics of the materials can be predetermined, monitoring the resonant frequency, amplitude or Q of the oscillating system provides a measure of the elasticity of the elastomer.

In accordance with the invention, changes in elasticity are related to changes in a parameter such as the resonance frequency, amplitude, or Q value of the piezoelectric oscillator. The piezoelectric materials in contact with the elastomer are used to drive a standard piezoelectric oscillator circuit. Since the piezoelectric materials' characteristics are predetermined, monitoring the frequency, amplitude or Q of the oscillator circuit provides a measure of elasticity. Changes in the resonant frequency, amplitude or Q value of the oscillator indicate changes in the elasticity of the elastomer.

DETAILED DESCRIPTION

The present invention is method and apparatus which use piezoelectric oscillators as elastomer degradation sensors, particularly as in situ sensors. A piezoelectric material is placed in contact with an elastomer to form an oscillating system. The piezoelectric may contact a surface of the elastomer or be embedded therein. The elastomer can be in situ in a piece of equipment or vehicle. The characteristics of the piezoelectric material, such as size, shape, and composition, and the elasticity of the elastomer determine the resonant frequency and other properties or parameters of the oscillating system. The resonant oscillation of the oscillating system is used to drive a simple electric oscillator circuit. The frequency of this oscillator circuit, and hence the resonant frequency of the oscillating system, is measured with standard frequency counting electronics. Changes in the resonance frequency of the oscillating system indicate changes in the elastic properties of the elastomer. Alternatively, other parameters of the oscillating system, such as amplitude or Q, can be measured, and changes in these parameters will also indicate changes in these parameters also indicate changes in the elastic properties of the elastomer.

Elastomer as used herein means any rubber or rubber-like material including but not limited to polyisoprenes, butadienes, styrenebutadienes, acylonitrile butadienes, polychloroprenes, isobutylene isoprenes, polysulfides, polymethanes, chlorosulfonated polyethylenes, ethylene propylenes, fluoroelastomers, polysiloxanes, polyesters, polymethanes, silicones, and the like.

Figure 1:
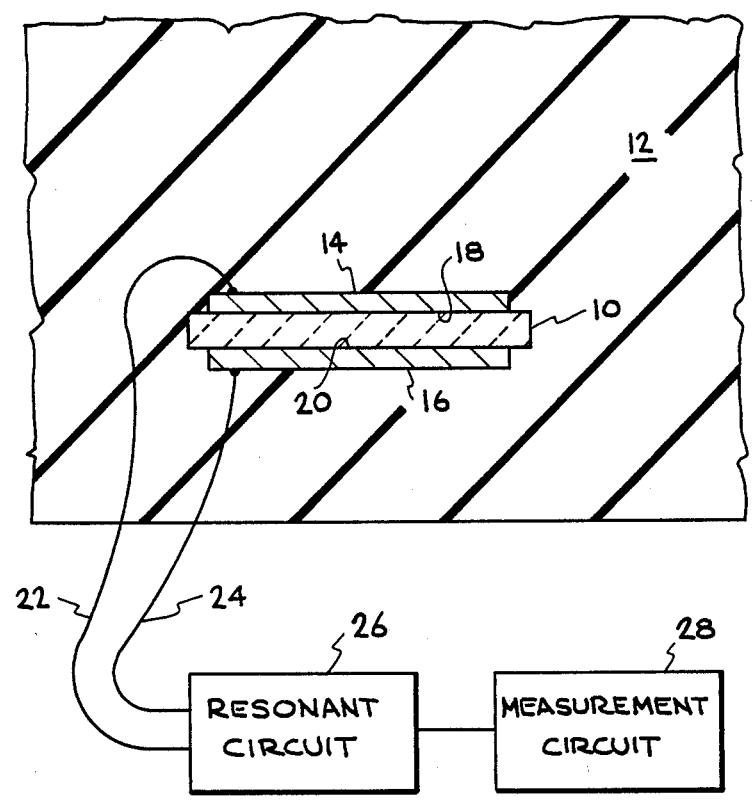
FIG. 1 diagrammatically illustrates placement of a piezoelectric material in an elastomer in accordance with a preferred embodiment of the invention.

FIG. 1 is a diagrammatic illustration of an apparatus according to the invention which shows the placement of a piezoelectric material in an elastomer. Piezoelectric material 10 is embedded in elastomer 12 which may be located in situ in equipment or a vehicle. Electrical contacts 14 and 16 are attached to faces 18 and 20 of piezoelectric material 10, respectively. Electrical leads 22 and 24 connect contacts 14 and 16 to the resonant circuit 26. Resonant circuit 26, together with piezoelectric material 10, form an oscillator circuit, which oscillates at the resonant frequency of piezoelectric material 10 embedded in elastomer 12. Measurement circuit 28 is connected to resonant circuit 26 to measure a parameter of the resonant circuit such as resonant frequency, amplitude or Q.

Figure 3A:
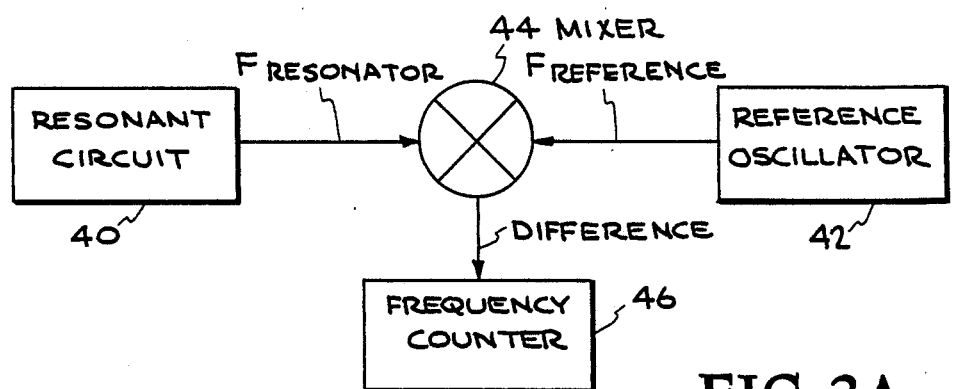
FIGS. 3A, B, C are schematic diagrams of a frequency shift detector, an amplitude shift detector, and an oscillator circuit, respectively.
Figure 3B:
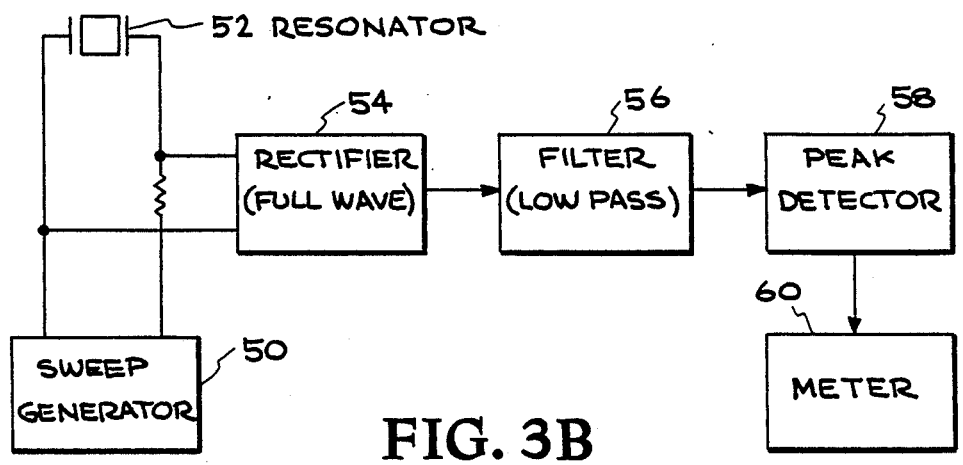

Measurement circuit 28 may be a frequency counter to measure the oscillation frequency of resonant circuit 26, or a Q-meter to measure the oscillator Q-value, or any other conventional measurement circuit. A spectrum analyzer could be used to observe all the variables at once. A mixer circuit, with a reference oscillator and a frequency counter to examine beat frequencies, could be used to monitor frequency. Such a frequency shift detector circuit is illustrated in FIG. 3A, in which the signal from resonant circuit 40 is combined with a signal from reference oscillator 42 in mixer 44, and the difference signal is measured by frequency counter 46. A simple peak height monitor with LED readout could be used to measure amplitude. Such an amplitude shift detector circuit is illustrated in FIG. 3B in which sweep generator 50 is connected across resonator 52 which is formed of the elastomer-piezoelectric system. The sweep generator 50 sweeps through the resonant frequency of the resonator and the oscillation amplitude is measured by passing the signal through full wave rectifier 54, low pass filter 56, peak detector 58, into meter (LED readout) 60.

Many different piezoelectric materials can be used in accordance with the invention, but for particular applications some may be more suitable than others. The material used in miniature microphones is generally suitable. Preferred piezoelectric materials include quartz and piezoelectric ceramics, such as those made of barium titanate. Quartz has very good temperature stability and very high Q values, which give rise to stable resonance frequencies and highly accurate determination of elasticity. Quartz tends to be brittle, add is therefore not suitable for some applications where it would be subjected to severe vibration or shocks. Barium titanate ceramics offer many advantages, and for some applications are the preferred piezoelectric material. They have very good chemical stability and possess high resistance to mechanical vibration and shock. They can be operated at temperatures up to 100° C. and can be exposed to very high temperatures without permanent destruction of their piezoelectric properties. Importantly, barium titanate ceramics have a polycrystalline structure; thus they can be shaped in complicated forms which would be difficult or impossible to obtain with single crystals. Another advantage of barium titanate is its low electrical impedance, which allows lower voltages to be used in resonant circuit 26.

The preferred shape of piezoelectric material 10 depends largely on the nature of the application. The sensors are typically small and can be placed in situ without affecting the machinery or vehicle in which they are placed. For example, small rectangles, e.g., 6.5 mm on a side and a few tenths of a millimeter thick, can be used. The sensor is placed in contact with the elastomer, either on a surface of the elastomer or embedded therein.

Figure 2:
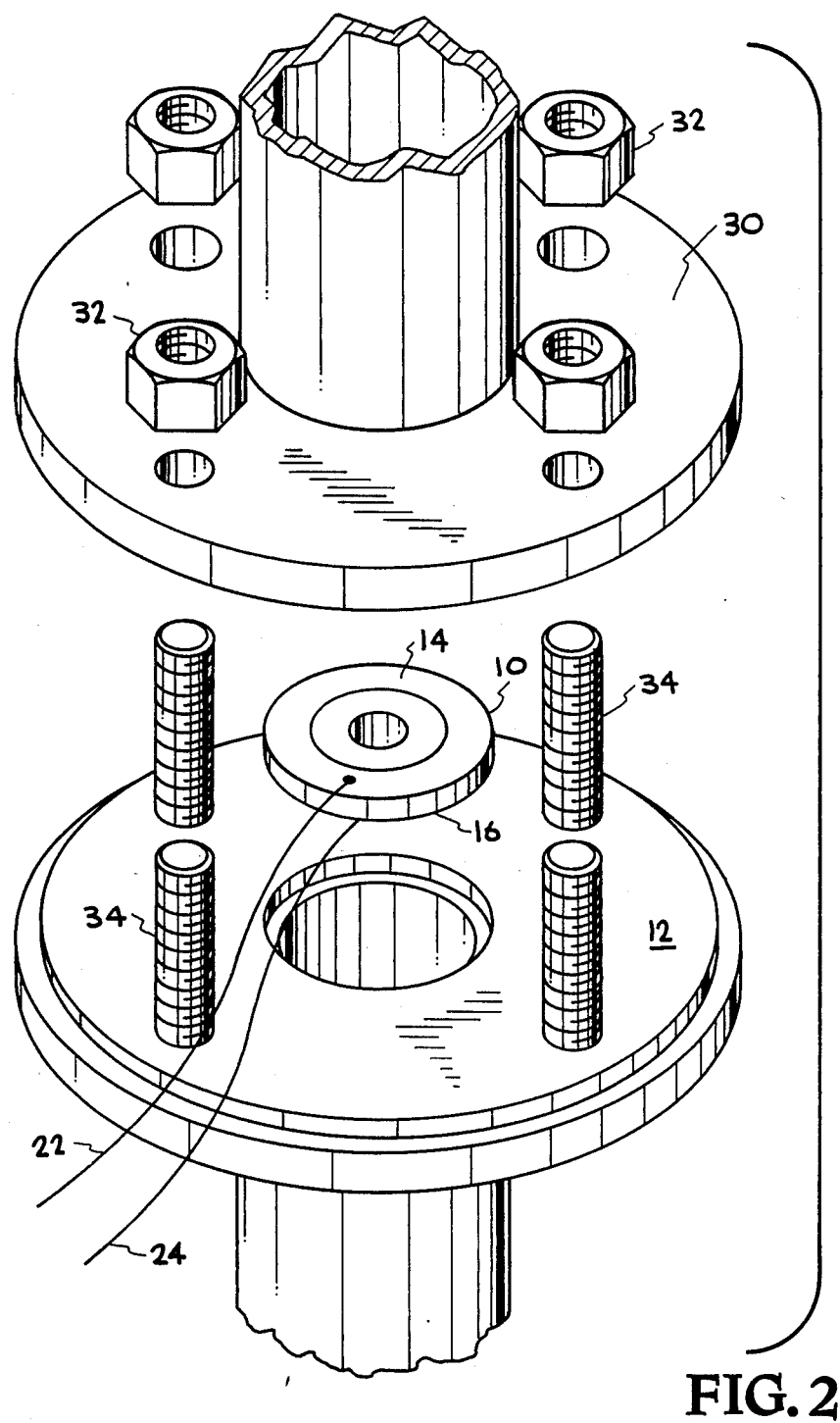
FIG. 2 diagrammatically illustrates an embodiment of the invention which employs a piezoelectric material in the shape of a washer.

FIG. 2 shows an application where piezoelectric material 10 is shaped like an annulus, or washer. In this application, the elasticity of flange gasket 12 is monitored by inserting piezoelectric material 10 and its associated contacts 14 and 16, and leads 22 and 24, between flange gasket 12 and flange 30. The mode of oscillation of piezoelectrical material 10 is selected so that displacements are directed against flange gasket 12 when nuts 32 are tightened down on studs 34. Associated contact 14 of piezoelectric material 10 is suitably insulated whenever flange 30 is made of conductive material.

Resonant circuit 26 is a standard crystal oscillator circuit, e.g., Holt, *Electronic Circuits: Digital and Analog* (John Wiley & Sons, New York, 1978) pgs. 748–752 discloses several crystal oscillator circuits suitable for use with the invention. Accordingly, the cited pages of Holt are incorporated by reference.

King, in U.S. Pat. No. 3,164,004 issued Jan. 5, 1965, entitled "Coated Piezoelectric Analyzers," also discloses crystal oscillator circuits suitable for use with the present invention. Accordingly, King is incorporated by reference for its description of crystal oscillator circuits.

Figure 3C:
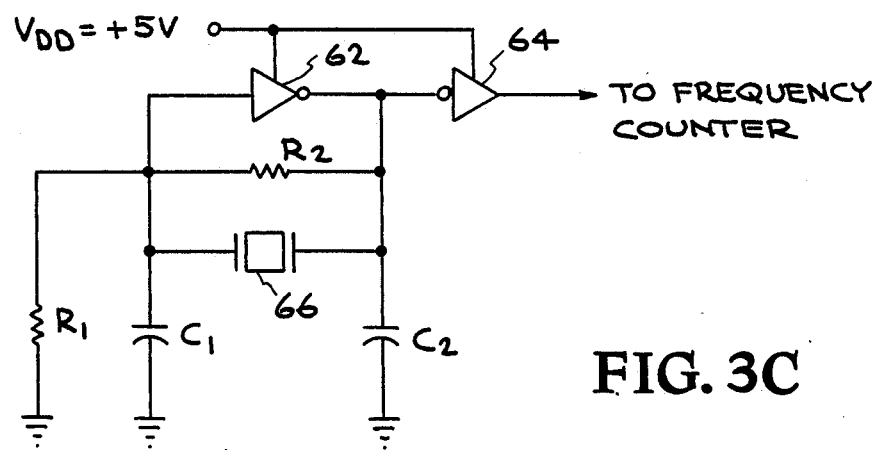

An illustrative oscillator circuit, shown in FIG. 3C, is formed of a pair of inverters, 62 and 64, connected in series with resonator 66 (elastomer-piezoelectric) connected between the input and output of inverter 62. In a particular embodiment IC's 62, 64 are SN74LS04 inverters, $C_1$ and $C_2$ are 1000 pF, $R_1$ is 22K and $R_2$ is 4.7K.

An experimental elasticity sensor was formed of a 6 Mhz barium titanate piezoelectric ceramic resonator 0.65 cm on a side and a few tenths of a millimeter thick. The casing was removed from the resonator and fine wire leads soldered to two corners of the ceramic square. The resonator was placed in intimate contact with the elastomer, i.e., sandwiched between two similar pieces of neoprene, gum, or silicone rubber measuring $1.9 \times 1.9 \times 0.15$ cm. Both new rubber samples and rubber samples that had been exposed to ozone-contaminated atmospheres (8 ppm for 7 hours) to simulate aging were used. The rubber-resonator sandwich was placed on a weight bench with various loads on the piston to provide pressures ranging from 78 to 203 g/cm$^2$. For some experiments, the entire weight bench was placed in an incubator and maintained at a temperature setting of either 40° or 55° C. The sensor was monitored remotely with a simple oscillator circuit and an HP3585A spectrum analyzer with tracking generator.

Figure 4:
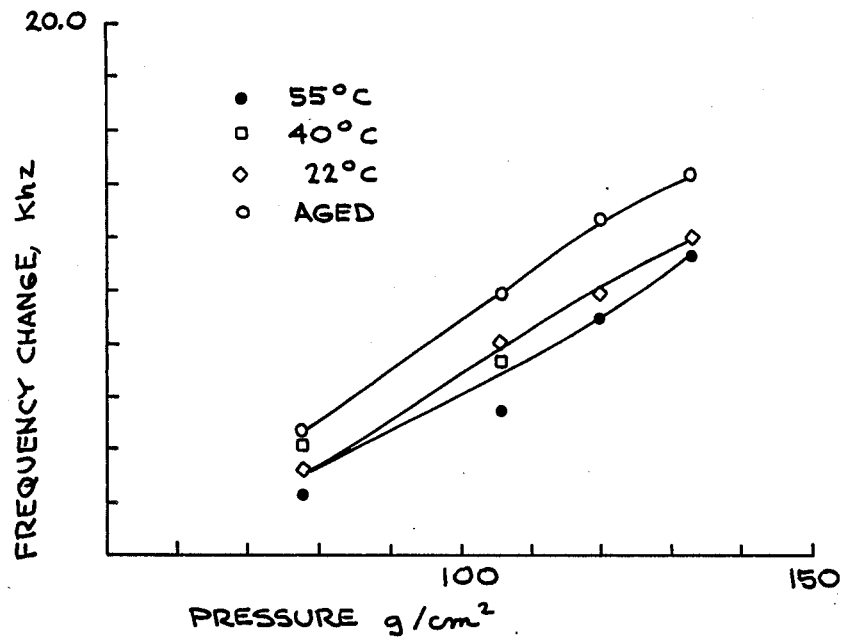
FIG. 4 is a graph of the change in resonant frequency as a function of pressure.
Figure 5:
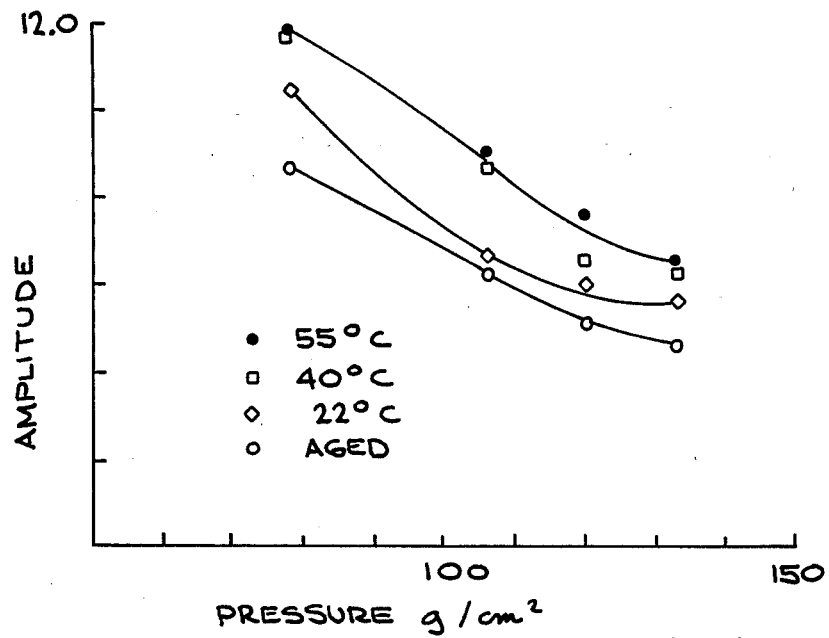
FIG. 5 is a graph of amplitude changes as a function of pressure.

The experimental observations included resonant frequency, amplitude, and "Q" value. Three types of experiments were conducted. In the first type, initial observations were made at room temperature (22° C.) with a rubber-resonator sandwich subjected to a pressure of 78 g/cm$^2$. The pressure was then removed from the sandwich for a period of five minutes to let the rubber relax. Next, a pressure was applied of 108 g/cm$^2$ on the sandwich (30 g added weight) and the observations were repeated, followed by a five minute period of pressure-free relaxation. This procedure was repeated with further pressure increases of 45 g/cm$^2$ and 60 g/cm$^2$. The entire set of experiments was repeated at 40° and 55° C., and at room temperature only, using the "aged" samples. As shown in FIGS. 4 and 5 for silicone rubber, there is a shift in resonant frequency and a reduction in amplitude with increased pressure (increased damping). Similar changes were observed for the other rubber types and for elastomer samples pretreated with ozone to simulate aging.

Figure 6:
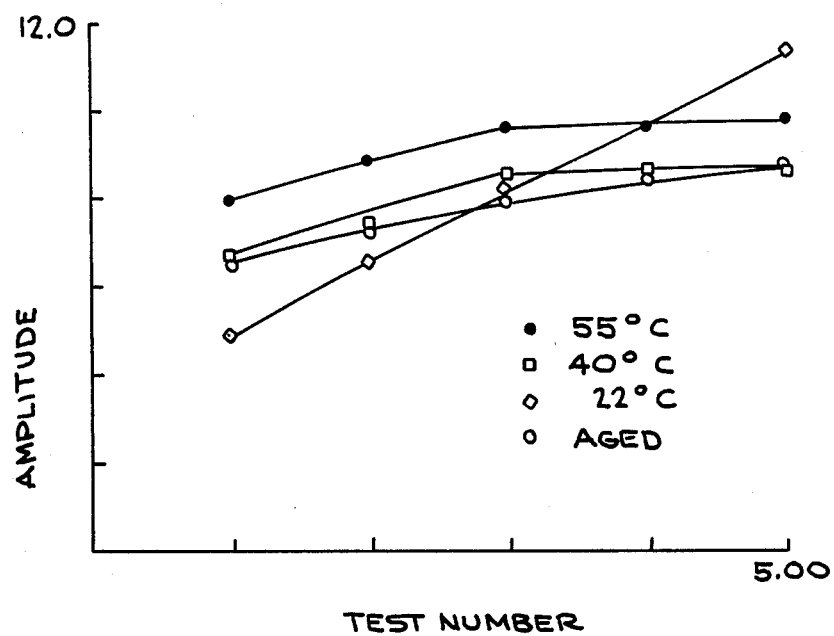
FIG. 6 is a graph of amplitude changes at fixed pressure showing the effects of sample fatigue caused by applying increased pressure between measurements.

In the second type of experiment, initial observations were made with a rubber-resonator sandwich subjected to the pressure of the weight bench only. Next, 100 g were added for a period of five minutes and removed; measurements were made immediately thereafter with only the pressure of the weight bench. This loading/unloading procedure was carried out with added weight in 50 g increments up to a total added weight of 250 g. These experiments were also performed at 40° and 50° C, and at room temperature only, using "aged" samples. FIG. 6 shows the effects of fatigue (increased signal amplitude) for neoprene rubber when the sandwiches were subjected to a pressure of 78 g/cm$^2$. Each of the samples exhibits reduced damping (increased amplitude) with repeated measurement.

Figure 7:
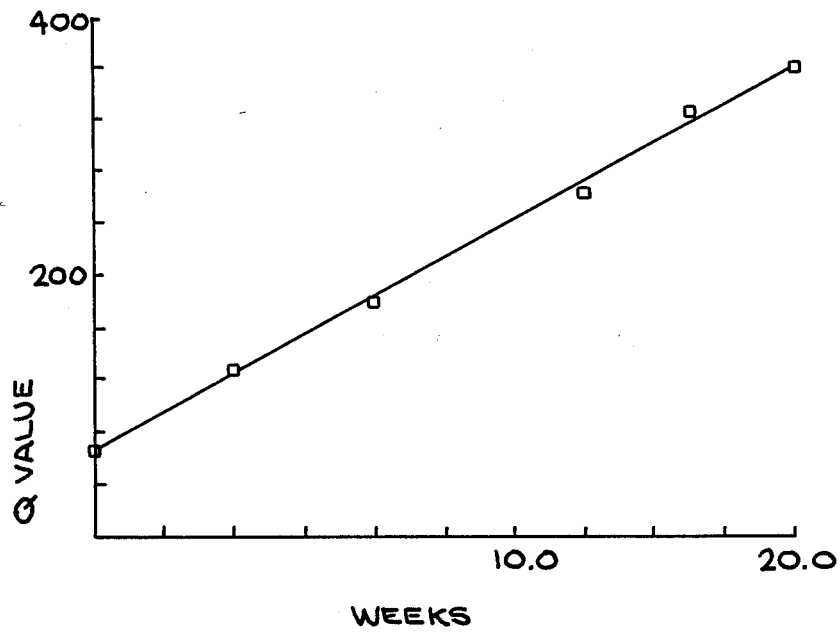
FIG. 7 is a graph of Q value as a function of time with the sample subject to constant pressure.

The third type of experiment involved placing a rubber-resonator sandwich on the weight bench with an added load of 100 g and making measurements over a period of five months. FIG. 7 shows the increase in "Q"value with time resulting from a constant pressure, indicating a decrease in damping (loss of elasticity) as the rubber fatigues.

The observed amplitude changes ranged from a few percent to more than 50%. The changes in resonant frequency, on the other hand, were only a few KHz out of 6 MHz and were difficult to evaluate accurately due to the shape of the damped curve. Quartz oscillators would provide greater "Q" values and might simplify the measurement process. The narrower resonance shape would be necessary to use a reference oscillator, mixer, and beat frequency counter as the electronic monitor. Quartz oscillators, however, are considerably less rugged than ceramic oscillators. Therefore, a ceramic oscillator and peak height monitor are preferred for an in situ elasticity monitoring system.

The description of the foregoing embodiments of the invention have been presented for purposes of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method of monitoring the degradation of an elastomer, the method comprising the steps of:
   contacting a piezoelectric material having associated electrical contacts with the elastomer to form an oscillating system, the piezoelectric material and associated contacts being part of an oscillator circuit;
   causing the oscillator circuit to oscillate;
   measuring a parameter of the oscillator circuit; and
   relating changes in the parameter of the oscillator circuit to the degradation of the elastomer.

2. The method of claim 1 wherein the parameter measured is the resonant frequency.

3. The method of claim 1 wherein the parameter measure is the amplitude.

4. The method of claim 1 wherein the parameter measured is the Q value.

5. The method of claim 1, wherein said piezoelectric material is a piezoelectric ceramic.

6. The method of claim 5, wherein said piezoelectric ceramic is made of barium titanate.

7. The method of claim 1, wherein said step of contacting includes embedding said piezoelectric material in said elastomer.

8. The method of claim 1 wherein the piezoelectric material is contacted with an elastomer which is located in situ in equipment or a vehicle.

9. Apparatus for monitoring the degradation of an elastomer, comprising:
   a piezoelectric material which is placed in contact with the elastomer;
   an oscillator circuit which is connected to the piezoelectric material and forms an oscillating system therewith;
   measurement means connected to the oscillator circuit for indicating degradation of the elastomer by measuring a parameter of the oscillating system.

10. The apparatus of claim 9 wherein the measurement means comprises means to measure the resonant frequency.

11. The apparatus of claim 9 wherein the measurement means comprises means to measure the amplitude.

12. The apparatus of claim 9 wherein the measurement means comprises means to measure the Q value.

13. The apparatus of claim 9 wherein the piezoelectric material is a piezoelectric ceramic.

14. The apparatus of claim 13 wherein the piezoelectric ceramic is barium titanate.

15. The apparatus of claim 9 wherein the piezoelectirc material is placed in contact with the elastomer in situ.

16. The apparatus of claim 9 wherein the piezoelectric material is embedded in the elastomer.

* * * * *